United States Patent [19]

Liss et al.

[11] Patent Number: 5,109,847
[45] Date of Patent: May 5, 1992

[54] NON-INTRUSIVE ANALGESIC NEUROAUGMENTIVE APPARATUS AND MANAGEMENT SYSTEM

[75] Inventors: Saul Liss; Bernard Liss; Ben Manor, all of Glen Rock, N.J.

[73] Assignee: E.P. Inc., Glen Rock, N.J.

[21] Appl. No.: 703,610

[22] Filed: May 21, 1991

[51] Int. Cl.⁵ ............................................. A61N 1/18
[52] U.S. Cl. ..................................................... 128/421
[58] Field of Search ......................................... 128/421

[56] References Cited

U.S. PATENT DOCUMENTS

| | | | |
|---|---|---|---|
| 3,902,502 | 9/1975 | Liss et al. | 128/422 |
| 4,305,402 | 12/1981 | Katims | 128/421 |
| 4,989,605 | 2/1991 | Rossen | 128/421 |

Primary Examiner—William E. Kamm
Assistant Examiner—Scott M. Getzow
Attorney, Agent, or Firm—Hopgood, Calimafde, Kalil, Blaustein & Judlowe

[57]  ABSTRACT

The present invention pertains to a portable non-invasive electronic apparatus which can be used to relieve pain or alter the symptoms of certain neurological dysfunctions. A specifically contoured constant current and current limited waveform is generated and applied to selectively positioned electrodes. A program controlled processor tracks usage of the unit to prevent abuse and monitor progress. An overall treatment regimen centered on the stimulator may be effected simply and safely.

10 Claims, 4 Drawing Sheets

CARRIER FREQUENCY
15,000 hz MONOPOLAR
FIG. IA
1st MODULATOR
15 hz
FIG. IB
2nd MODULATOR
500 hz
FIG. IC
TYPICAL COMBINED
WAVEFORM (MONOPOLAR)
FIG. ID
TYPICAL COMBINED
WAVEFORM (BIPOLAR)
FIG. IE

NON-INTRUSIVE ANALGESIC NEUROAUGMENTIVE APPARATUS AND MANAGEMENT SYSTEM

The present invention generally relates to an apparatus that modulates the neurological responses associated with certain biological dysfunctions and neural pain, pain caused by blood flow deficiency and more specifically, an apparatus and system for the controlled management of treatment of selected pain and/or neural dysfunction induced maladies.

BACKGROUND OF THE INVENTION

The sensation of pain is associated with numerous physiological and psychological ailments and is a universal experience of all complex living organisms. Pain, as the mental manifestation of a neurological response, is an important biological attribute and critical to living and adapting to the environment. Notwithstanding this important role, the alleviation of pain has been a fundamental goal of medicine for as long as the medical profession has existed. Indeed, the ability to control the neurological pathways through which pain is conveyed, has made complex procedures far simpler to implement and much less traumatic to the patient.

There is additionally a class of neurological response which is associated with pain that does not correspond to or act as a warning for a particular physical damage or biological dysfunction. In fact, many biologically important transitions are characterized by significant pain, such as the withdrawal period of an addict, during which time the addict's system is depleted of a specific endogenous narcotic. Other mental conditions which are neurological response dependent conditions include depression, hypertension, causalgia pain, insomnia and jet lag.

The importance of the ability to control neurological response and associated perceptions of pain and distress has led to the development of many pain control methodologies. The most common of which employs bioactive chemical agents that act to block neural transmission pathways within the body. These are designed to operate locally for spot treatment or broadly for generalized control or inhibition of pain response throughout the body. Chemical interference with pain signals has broad based appeal, but in many instances is unacceptable. For example, certain chemicals have toxic side affects or cause allergic reactions to certain patients. For more chronic ailments, such as chronic migraine headache syndrome, continuous absorption of chemical narcotics may reduce the associated pain, but at unacceptable high costs associated with interference with routine activities, addiction and/or toxicity of the narcotic.

In view of the problems associated with chemical pain control, efforts have abounded to discover treatment approaches which would not involve pharmacological (chemical) interference with neural transmitters in the body. One approach that has recently sparked tremendous interest is the use of low power electrical stimulator devices capable of passing currents across key neural transmitter junctions in the body and thus effecting a blockage of neurological pathways which are inducing messages of pain to the brain. A practical implementation of this approach is disclosed in U.S. Pat. No. 3,902,502 to Liss, et al; the teachings of which are herein incorporated by reference.

The system disclosed in the '502 patent presented a pulsed direct current waveform having a high frequency carrier modulated by a single low frequency modulation. It was discovered that this waveform was particularly successful at controlling symptoms of certain neurological disorders.

Although effective for its applied treatment, many electrical stimulatory devices are limited to certain applications and lack the requisite flexibility for broad-based appeal. In addition, a drawback to the use of electrical stimulation to control pain is the concern by patients and others about the impact of power dissipation on the patient. Although low current, the power dissipation of many of the electrical stimulation devices is still quite significant. Efforts to reduce the applied power have resulted in stimulation devices with little or no physiological impact.

There has been, therefore, a search for new electrical stimulation devices characterized by exceptional pain management capabilities while reducing the overall patient exposure to electrical energy. The present invention is a result of this search.

SUMMARY AND OBJECTS OF THE PRESENT INVENTION

This invention may be summarized, at least in part with reference to its objects.

It is, therefore, an object of the present invention to provide an apparatus for the selective generation of low current nerve stimulation waveforms configured to control pain and/or reduce the specific symptoms of certain neurological dysfunctions.

It is another object of the present invention to provide an apparatus for generating a complex waveform that when applied to a patient involves very low power dissipation.

It is a further object of the present invention to provide a pain control system that includes a means for creating a complex waveform and a data processing means for managing and recording the implementation of that waveform.

It is yet another object of the present invention to provide a method for low power, electrically induced analgesic treatment by the placement of at least two electrodes on selected neurologically important sites and the controlled introduction of a complex waveform for a predetermined time forming a treatment regimen.

It is still another object of the present invention to provide a method for treating the neurological dysfunctions associated with such ailments as migraine headaches, dental procedures, PMS and drug withdrawal.

The above and other objects of the present invention are realized in a specific illustrative electrical stimulator device. This device includes a small DC power source and a means for converting the current output of the power source into a complex waveform as an output across two or more electrodes attached to the patient's body. The complex waveform includes a carrier frequency with at least two low frequency modulations. The carrier frequency will range between 1 and 100,000 kilohertz. The first modulation to this carrier will have a frequency between 0.01 and 199 kilohertz. The second modulation to the carrier will have a frequency range between 0.1 and 100 kilohertz. Each modulation to the carrier is a pulse train in the form of a square waveform.

The placement of the electrodes will depend on the ailment of the subject of treatment, and the frequency of treatment will depend on the severity of the pain or dysfunction.

In accordance with the varying aspects of the present invention, the stimulator device may include a digital data processor and stored programming for enhanced implementation of the prescribed treatment. In this manner, the program controlling the output of the stimulator will prevent use beyond a number of times and beyond the time set for each use. The limits of number of uses and of length of time for each use will be set by the prescribing physician. This promotes and enhances the use of expressly developed treatment regimens by a prescribing physician. The patient's progress can be compared to patient compliance in the context of continuing the prescription or altering same on behalf of the patient.

The foregoing features of the present invention may be more fully understood in view of a specific illustrative embodiment thereof presented hereinbelow in conjunction with the following drawings of which:

BRIEF DESCRIPTION OF THE FIGURES

FIG. 1 is a representation of a sample waveform utilized in the present invention;

DESCRIPTION OF THE PREFERRED EMBODIMENT

Figure 2:
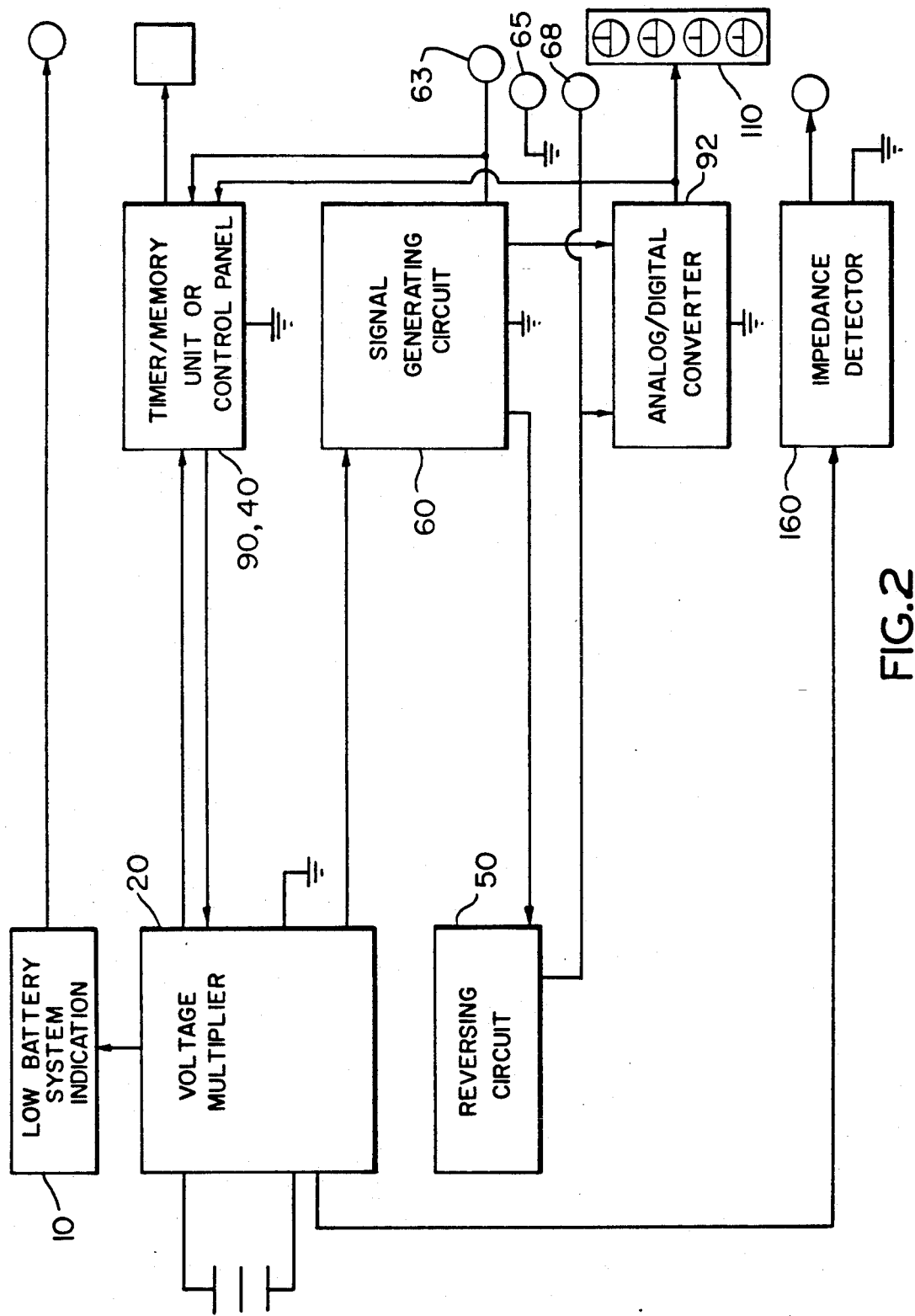
FIG. 2 is a block diagram of the inventive apparatus for generating the waveform depicted in FIG. 1.

Discussing the present invention first in overview, it is a fundamental diserratum to provide a portable non-invasive analgesia inducing apparatus that exhibits a selectively developed complex waveform for an electrical output. This output is applied between at least two contact probes for generating intracorporal current. The placement of the probes will depend on the treatment regimen. For example, migraine headache syndrome may involve the placement of the contacting probes on each side of the patient's cranium, one at the primary site of pain and the second at the contralateral trapezius insertion. Other locations may include intra-oral e.g., for local analgesia to control the pain associated with a dental restoration procedure.

Although the theory describing the underlying pain control phenomenon is not well known or, for that matter, even established, it is generally believed that the introduction of an intracorporal current acts upon the electrically conducted neural transmitters of the patient. It has been discovered that the particular complex waveform of the present invention when applied to a patient creates distinct changes in the blood plasma and cerebral spinal fluid concentration of such compounds as melatonin, serotonin, beta endorphin, norepinephrine and cholinesterase which are highly correlated with the pain/pleasure centers of the central nervous system.

In operation, the present invention involves two functional attributes. The first involves the generation of the complex waveform of a select signature. The second attribute is directed to the implementation of the treatment in a delineated treatment regimen.

With the above overview in mind, attention in first directed to FIG. 1 which presents the various components of the complex waveform of the present invention. More particularly, and starting with FIG. 1A, a graphical representation is provided of the carrier frequency for one specific time segment. In this representation, the carrier frequency equals 15 kilohertz. The amplitude is volts (DC) and a duty cycle of 50%. The waveform contains 25 bursts of 15 pulses for each burst. The period for each burst is 2 milliseconds and the period for each pulse is 66.7 microseconds. For each, the burst and the pulse, the duty cycle is 50% on time. Continuing in FIG. 1, FIG. 1B presents the first modulation to the carrier frequency. In this example, the first modulation has a frequency of 15 Hertz and a duty cycle of 0.75. The second modulation is depicted in FIG. 1C. The second modulation has a frequency of 500 Hertz and a 50% duty cycle. Continuing through FIG. 1 and specifically FIG. 1D, the waveform combining the components depicted in FIGS. 1A through C above is presented.

The complex waveforms of the present invention may be generated with sinusoidal, sawtooth, hyperbolic or other wave shapes; for clarity, the waveforms presented in FIG. 1 and further discussed below have been exemplified by a simple square wave.

A cycle for the waveform will consist of 50 milliseconds "on" time in which the pulses for that frequency combination are generated and then there will be an "off" time of 16.7 milliseconds.

Finally, in FIG. 1E, a complex waveform according to the present invention is provided, wherein the polarity of the output is switched from positive to negative on a periodic basis, e.g., 67 milliseconds. This is contrasted with the waveform of FIG. 1D in which the polarity remains positive throughout the cycle; the pulsed DC waveform of FIG. 1D is considered a monopolar output while the output depicted in FIG. 1E is considered bipolar.

For purposes of rough approximation, the energy dissipation in using the present invention is represented by the area under the pulses depicted in FIG. 1D. It can, therefore, be recognized that by adding the second modulation, having a 50% duty cycle, results in a 50% decrease in power dissipation.

The circuit is presently provided with one of the following frequency combinations but not limited to:

1) 15 Hz, 500 Hz, 15,000 Hz - Monopolar;
2) 15 Hz, 500 Hz, 15,000 Hz - Bipolar (7.5 Hz);
3) 15 Hz, 500 Hz, 60,000 Hz - Monopolar; or
4) 15 Hz, 4,000 Hz, 60,000 Hz - Monopolar.

Turning now to FIG. 2, the functional elements of the inventive device are presented. The power source to the present system will either be a battery having nominal 9 volt terminal voltage or some rectified and properly transformed line (AC) power source. The battery provides the basic DC power source for generating the complex waveform. This is channeled and controlled by the voltage multiplier 20. The output of the voltage multiplier 20 which is between 27 v to 40 v, is fed to signal generating circuit 60 which is the oscillating circuit that converts the constant DC output into the complex waveform having the desired characteristics.

The specific constant current and current limited waveform generated by signal generating circuit 60 is pre-set by entering the various frequency settings for the two modulations, and the carrier. This may be entered manually through adjusting the settings on control panel 90. Alternatively, these settings may be stored in digital memory 40 as previously set values. The actual output of this system is regulated by monitor 70 which then provides the system output on a display, via control panel 90, or a memory value for subsequent retrieval from memory 40.

The signal generating circuit 60 receives the voltage of 27 v to 40 v from the voltage multiplier. Within the signal generating circuit 60, the voltage branches off into a carrier frequency and two modulation frequencies. An example of the branching of the waveform is described in FIG. 1.

In FIG. 2, the system supports two separate probes for placement on the patient. Probe 63 represents the positive terminal as generated by signal generating 60. The second probe 65, is grounded within the circuit. For operation applying a bipolar waveform, the probes are connected to terminal 65 and 68, respectively. Terminal 68 is the output from reversing circuit 50, which may be present and which acts to flip the signal generating circuit pursuant to pre-set timing constraints.

The following ancillary systems are also present in this circuit. The low battery and system on indicator 10 which monitors the battery output via voltage multiplier 20 generates an alarm signal when battery output voltage drops below the preset limit, say 7.0 volts. It also shuts the system down if the output voltage falls below the present limit of approximately 6.0 volts.

The analog/digital converter 92 converts the signal from the signal generating circuit 60 so that the patient can read it. The analog/digital converter 92 reads the level of output and converts it to the appropriate signal for the four gate integrated circuit which uses that signal to turn on the appropriate sequence of four LEDs 110.

Finally the impedance detector 160 is used to determine if the system is being used on a person (as opposed to someone just running the system without attaching it to a person).

Figure 3:
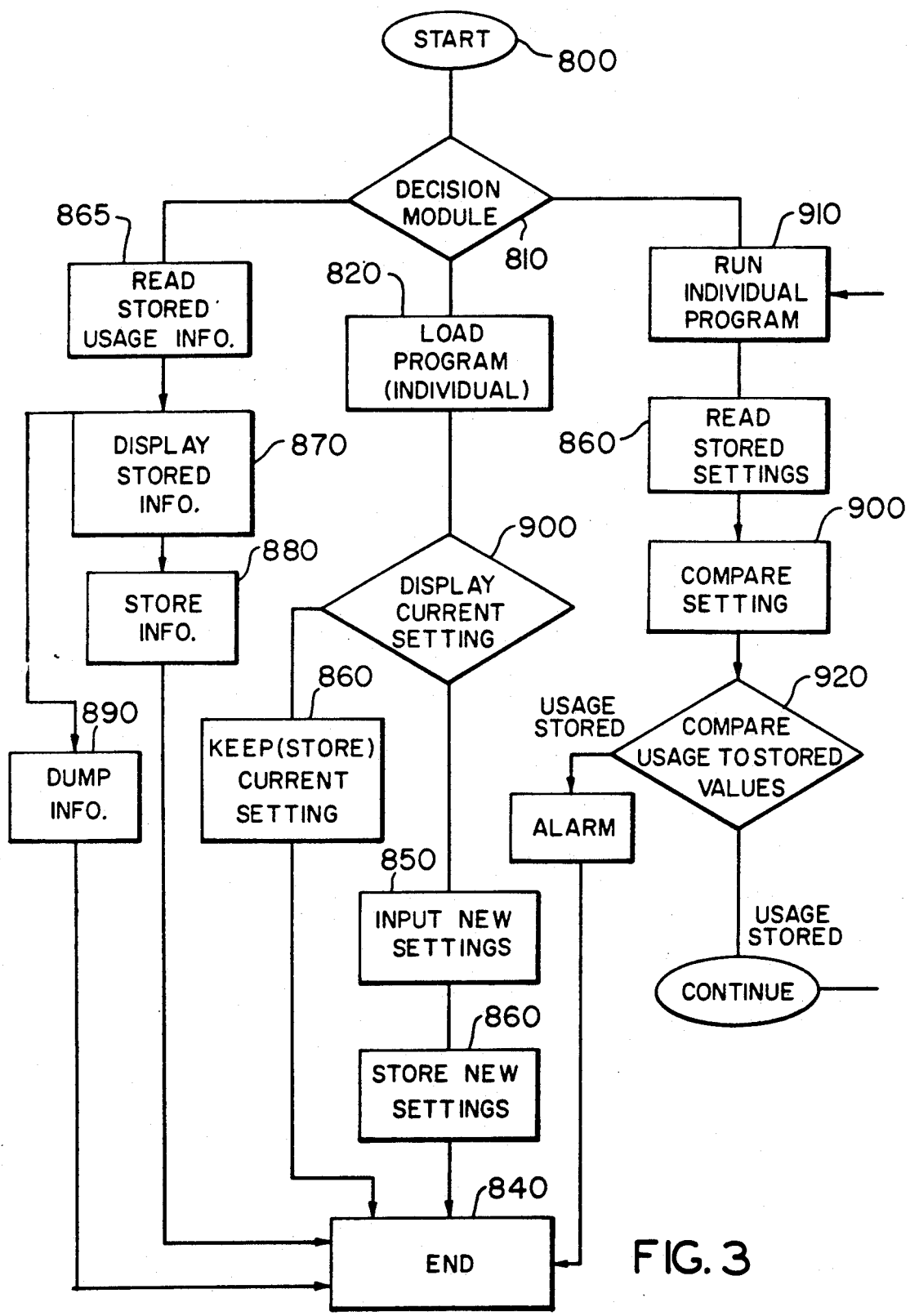
FIG. 3 is a logic flow chart of the data processing program controlling the operation of the apparatus of FIG. 2.

Referring now to FIG. 3, which is a flow chart of the timer unit 90 which the apparatus will use to monitor usage by the patient. This program will prevent the patient from misusing the apparatus and will allow the physician to set an individual treatment program and to monitor the patient's compliance to the set program.

The timer unit 90 will allow the therapist to set the number of days the system is to be used, the number of times per day the system will be used and the time duration for each use.

The program will start 800 with an Origination Decision module 810. The Origination Decision Module 810 will give the therapist three choices for use. If the Individualized Program 820 pathway is chosen, the timer unit will load the Individualized Program 820. Then the Individualized Program 820 will begin with a display showing the Current Setting 900, for each of the parameters (i.e. the number of days of use, the number of times per day of use and the length of time for each use). Next the program will ask the therapist whether he wants to Keep the Current Settings 900, or Input New Settings 830. If the therapist wishes to use the same settings as are already registered in the program, the Individualized Program 820, will Store 860 the values and will End 840. However, if the therapist wishes to change the settings, the program will proceed to the Change Input Values 850 module in which the computer will ask the therapist for the new values for the settings. Then the computer will Store 860 the new values and will End 840.

Another selection which a therapist may make at the Origination Decision Module 810 is to read the stored information from the patient's system. If the therapist decides to access the Read Stored Results 865 module, the Setting and Use information will be displayed 870, and the therapist will decide whether to store the patient information in the Patient Storage Module 880, or else it will Dump the information 890 and it will End 840.

A final selection which the therapist may access through the Origination Decision Module 910, is actually to use the system. If this choice is the inputted selection, the Run Timed Program 910 will be initialized. The Run Timed Program 890 will read the stored 860 values. Then the program will Check 920 the Stored 860 values against the Current Running Settings 900 which is the values of the Run Timed Program 890 for this usage of the system. If the Current Running Settings 900 for the number of days of use is greater than the Stored 860 values, the program will End 840 without the system being turned on. Next, the Run Timed Program 890 will check the value of the Stored 890 values for the number of uses for a given day and if the Current Running Settings 900 is greater than the Stored 890 values for number of uses for a day, the system will End 840 for that day and the system will not be able to be used until the next day. Finally, as the system is being used, a Running Time Clock will be compared to the Run Timed Program, 890, and when the Current Running Settings in 900 is greater than the Stored 890 values for the length of time for that session, the system will End 840 for that session and the system will not be able to be used until the next session period.

Figure 4:
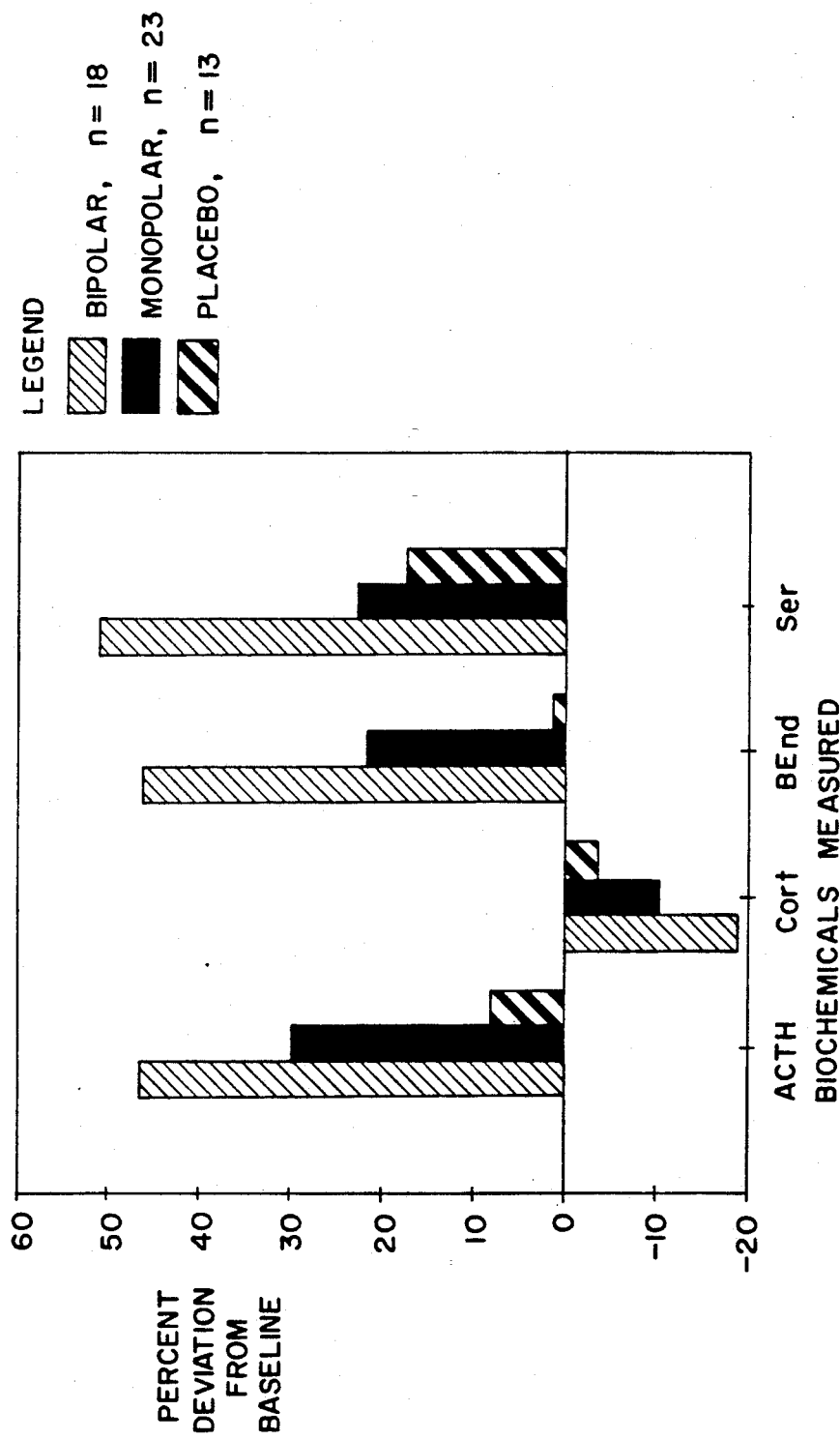
FIG. 4 is a chart of the effect of the inventive apparatus on certain neurotransmitters.

In FIG. 4 the chart demonstrates the effect of the inventive apparatus on the ACTH, cortisol, beta endorphin and serotonin, biochemical neurotransmitters. Multiple tests were made on three normals and other normal volunteers in the office using monopolar, bipolar and placebo instruments on a double blind basis. The symbol "n" denotes how many samples were made for each type of test. All tests for two of the three normals were made at the same time of day, the third normal was done always at 8 a.m. each morning and the 10 volunteers were processed at 10 a.m. to 12 noon for all their testing.

As is shown in the chart, the results on the tested neurotransmitters were marked. In each, the bipolar application had the greater effect on the neurotransmitter, with the monopolar still having significant results in its own right.

The embodiment of the above description has been based on discrete components to enhance the understanding of the functional characteristics of the system. Numerous modifications and adaptations thereof will be readily apparent to those skilled in the art without departing from the spirit and scope of the present invention.

What is claimed is:

1. In combination, in a system for the treatment of certain neural responsive conditions, said system comprising:
   a. means for generating a substantially constant current pulsed DC output voltage;
   b. means for converting said output voltage into a double modulated output adjustable constant current waveform;
   c. means for directing said double modulated output waveform across at least two contacts;

wherein said double modulated output waveform comprises a first waveform component ranging between 1 and 100.000 KHz, a second waveform component ranging between 10 and 199,000 Hz, and a third waveform component ranging between 100 and 100.000 Hz and each waveform component is substantially time invariant and distinct from said other waveform components.

2. The system of claim 1 wherein said first waveform component has a 50% duty cycle, and said second waveform component has from about a 50% duty cycle to about a 75% duty cycle.

3. The system of claim 2 further comprising a means for intermittently reversing polarity of said double modulated waveform.

4. The system of claim 2 wherein said first waveform component is approximately 15,000 Hz, said second waveform component is approximately 15 Hz and said third waveform component is approximately 500 Hz.

5. In combination in a method for the treatment of pain or symptoms of neural dysfunction distress comprising the steps of:
 a. developing a treatment regimen comprising a series of individual treatment sessions;
 b. programming a double modulated waveform generator with said treatment regimen;
 c. monitoring and recording an implementation of said treatment regimen with said double modulated waveform generator; and
 d. replaying a historical account of said treatment regimen for review;
wherein said double modulated waveform generator comprises a voltage regulator means, signal generator means, and at least two contacts for expressing a double modulated waveform.

6. The method of claim 5 wherein said double modulated waveform further comprises a first component above 4,000 Hz, a second component ranging between 0.5–400 Hz, and a third component between 100–4,000 Hz.

7. The method of claim 5 wherein said second component has a duty cycle above 50%.

8. The method of claim 6 wherein said double modulated waveform generator is portable and programmed for home use.

9. The method of claim 5 wherein said double modulated waveform generator further includes an abuse preventing circuit that automatically stops any waveform output when usage exceeds programmed limits.

10. The method of claim 5 wherein said double modulated waveform is applied across at least two body contact points to develop an intracorporal current.

* * * * *